US011946865B2

(12) United States Patent
Petisce et al.

(10) Patent No.: US 11,946,865 B2
(45) Date of Patent: Apr. 2, 2024

(54) SYSTEMS AND METHODS FOR NORMALIZING SIGNALS IN BLOOD CULTURE MEASUREMENT SYSTEMS

(71) Applicant: BECTON, DICKINSON AND COMPANY, Franklin Lakes, NJ (US)

(72) Inventors: James R. Petisce, Westford, MA (US); Robert E. Armstrong, Hunt Valley, MD (US); David J. Turner, York, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 286 days.

(21) Appl. No.: 17/254,794

(22) PCT Filed: Jun. 24, 2019

(86) PCT No.: PCT/US2019/038712
§ 371 (c)(1),
(2) Date: Dec. 21, 2020

(87) PCT Pub. No.: WO2020/005823
PCT Pub. Date: Jan. 2, 2020

(65) Prior Publication Data
US 2021/0262936 A1 Aug. 26, 2021

Related U.S. Application Data

(60) Provisional application No. 62/691,155, filed on Jun. 28, 2018.

(51) Int. Cl.
*G01N 33/49* (2006.01)
*A61B 5/00* (2006.01)
(Continued)

(52) U.S. Cl.
CPC ....... *G01N 21/6428* (2013.01); *A61B 5/0071* (2013.01); *C12M 41/34* (2013.01);
(Continued)

(58) Field of Classification Search
None
See application file for complete search history.

(56) References Cited

U.S. PATENT DOCUMENTS

| 4,255,053 A | 3/1981 | Luebbers et al. |
| 4,632,807 A | 12/1986 | Marsoner et al. |

(Continued)

FOREIGN PATENT DOCUMENTS

| JP | 2011512159 A | 4/2011 |
| WO | WO 1989/007757 A2 | 8/1989 |
| WO | WO 2023/154673 A1 | 8/2023 |

OTHER PUBLICATIONS

Extended European Search Report dated Apr. 7, 2022 for EP Application No. 19826765.0 in 7 pages.
(Continued)

*Primary Examiner* — Neil N Turk
(74) *Attorney, Agent, or Firm* — Knobbe Martens Olson & Bear LLP

(57) ABSTRACT

Systems and methods for optimizing detection of optical signals indicating the presence of an analyte of interest in a blood sample are described. In one aspect, a blood culture test vial having a sensor is inoculated with the blood sample, light at an excitation frequency of the sensor is transmitted to the test vial, an intensity of a plurality of fluorescence signals emitted from the test vial is measured, and the plurality of measured fluorescence signals are normalized using by a reference signal that is not dependent on a measured intensity of a fluorescence signal emitted from the test vial. In another aspect, a measurement system measures
(Continued)

fluorescence signals from one or more reference vials performing in extreme pH conditions. Fluorescence signals emitted from test vials inoculated with samples under test are measured and compared to the signals measured from the one or more reference vials to address or mitigate variability in hardware components of the measurement system.

11 Claims, 7 Drawing Sheets

(51) Int. Cl.
    *C12M 1/34*     (2006.01)
    *G01N 21/64*     (2006.01)
    *G01N 21/80*     (2006.01)

(52) U.S. Cl.
    CPC ............ *C12M 41/36* (2013.01); *C12M 41/38* (2013.01); *C12M 41/46* (2013.01); *G01N 21/80* (2013.01); *G01N 33/49* (2013.01)

(56) References Cited

U.S. PATENT DOCUMENTS

| | | | |
|---|---|---|---|
| 5,266,486 A | | 11/1993 | Fraatz et al. |
| 5,280,548 A | | 1/1994 | Atwater |
| 5,366,873 A | * | 11/1994 | Eden ...................... C12M 41/46 435/808 |
| 5,372,784 A | * | 12/1994 | Morris ................... G01N 21/78 436/167 |
| 5,770,394 A | * | 6/1998 | Berndt ................... G01N 33/52 435/808 |
| 6,046,055 A | | 4/2000 | Wolfbeis et al. |
| 6,080,574 A | | 6/2000 | Berndt |
| 2005/0068534 A1 | * | 3/2005 | Kleinfeld ............. G01N 21/645 356/417 |
| 2008/0188725 A1 | | 8/2008 | Markle et al. |
| 2010/0068755 A1 | | 3/2010 | Walsh et al. |
| 2011/0029252 A1 | | 2/2011 | Beaty et al. |
| 2011/0275112 A1 | * | 11/2011 | Sarver, Jr. ............. C12M 41/34 435/287.5 |
| 2012/0142115 A1 | | 6/2012 | Banks et al. |
| 2015/0185225 A1 | | 7/2015 | Edney et al. |
| 2016/0116408 A1 | | 4/2016 | Kahlman et al. |
| 2016/0122698 A1 | * | 5/2016 | Suslick ................... C12Q 1/04 435/288.1 |
| 2016/0209432 A1 | | 7/2016 | Reed et al. |
| 2017/0023555 A1 | | 1/2017 | Ou et al. |
| 2017/0144161 A1 | | 5/2017 | Hindson et al. |

OTHER PUBLICATIONS

International Search Report and Written Opinion dated Oct. 2, 2019 in International Application No. PCT/US2019/038712.

* cited by examiner

SYSTEMS AND METHODS FOR NORMALIZING SIGNALS IN BLOOD CULTURE MEASUREMENT SYSTEMS

CROSS REFERENCE TO RELATED APPLICATION

This application is a U.S. National Phase Application of PCT International Application No. PCT/US2019/038712, filed Jun. 24, 2019, which claims the benefit of U.S. Provisional Application No. 62/691,155, filed Jun. 28, 2018, each of which is hereby incorporated by reference in its entirety.

BACKGROUND

Field

The present disclosure relates to optimizing fluorescence detection systems, such as but not limited to optical blood culture measurements systems. More particularly, the present disclosure relates to systems and methods for normalizing fluorescence signals in an optical blood culture measurement system configured to detect the presence of an analyte of interest in a sample.

Description of the Related Art

In certain fields (e.g., medicine, pharmaceuticals, the food industry), quick and accurate determination of microorganism contamination in a particular system (e.g., a patient's blood, a batch of drug product, a food supply) is desirable. Methods employing sensors including fluorescent materials in conjunction with indicator materials have been developed for indirectly detecting microorganisms in a sample through their biological activities. Measurement systems employing these methods utilize fluorescent sensors or detectors for detecting fluorescent signals emitted from a container or vial housing the sample and sensor. Software and/or hardware systems are then utilized for processing data collected by the detectors. Signals measured by the detectors may be normalized using one or more reference signals, for example, to improve a signal-to-noise ratio in the resulting data measurements. In certain applications, an initial detector reading is taken when a vial is placed within a measurement system, and the initial reading is used as the reference signal. Normalization based on an initial detector reading may be subject to several limitations.

In some systems, an output of the measurement system at any particular time is generated based on a ratio of a current detector reading to an initial detector reading taken at the time the vial is first placed in the system (also referred to as "time zero"). In these systems, the current detector readings are normalized by dividing the current detector readings by the initial detector reading at time zero. Defining the detector reading at any time as $i_{reading}$, the initial detector reading as $i_{reading\ \#1}$, and the time that the initial detector reading is taken as $i_{reading\ \#1}$, the variability of the reported measurement system reading provided to the end-user can be described by the following equation:

variability of reported measurement system reading=$\Delta (i_{reading}/i_{reading\ \#1})+\Delta t_{reading\ \#1}$. As shown in this equation, a component contributing to the variability of the reported measurement system reading is any variability of the initial system reading designated as "$i_{reading\ \#1}$." This variability can reduce the sensitivity of the measurement system. For example, to distinguish that a change in output signal readings from a test sample are the result of the presence of a microorganism instead of the result of detector variability, greater changes in the output measurements may be required. In other words, detector variability may affect a threshold measurement required for determination of the presence of an analyte in a sample.

Additionally, there is often a delay between the time the sample is collected and injected into a test vial and the time the vial is placed in the measurement system. In some cases, the inoculated vial is placed within the measurement system after a number of hours or even a number of days, for example over a weekend. This means the initial detector reading may not be taken for 24-72 hours after the vial has been inoculated with the sample. The time period between when the sample is placed in the vial and when the vial is placed into the measurement instrument is commonly referred to as Delayed Vial Entry (DVE). The DVE time period may allow for the growth of bacteria or other microorganisms prior to placement of the vial within the measurement system. The growth of bacteria or other microorganisms prior to placement in the measurement system may affect the initial detector reading reference signal and, consequently, the test data normalized using the initial detector reading reference signal.

There are other drawbacks associated with using an initial detector reading as a reference signal to normalize current detector readings outputted by the measurement system. An initial detector reading reference signal may be affected by sensor temperature fluctuations. Ambient sensor temperature fluctuations can be caused by external factors such as inadequate control of the ambient environment by the end-user of the sensor and/or sensor equipment, changes in vial temperature after entry into the system, and air movement through the measurement system. Sensor temperature fluctuations may require compensation to provide accurate readings.

Current measurement and data processing techniques may also result in delayed detection of the presence of an analyte of interest. Signal changes from noise sources (user interaction, temperature changes, etc.) can appear to be organism growth. Algorithms used to process the detector data may use moving averages to compensate for these signal changes. Smoothing the signal using moving averages can reduce the random noise, but may also delay detection of signal changes caused by organism growth. Optical blood culture sensor systems must also distinguish impulse noises (such as bottle movements and drawer slams) from organism growth, so algorithms that process detected signals in these systems employ some forms of delay to ensure measured signal changes are sustained. Such sustained signal changes are more likely to occur when the signal changes are due to organism growth in the blood culture bottle rather than impulse noises. This built-in delay, however, can contribute to longer wait times from the time a sample is collected to the time a blood culture test result is generated.

Current normalization techniques also fail to provide real time feedback on measurement system signal quality. The system architecture of a measurement system may cause erroneous measurements to be made. For example, some light source components for exciting fluorescent materials within the sensor may degrade in emission intensity during their useful life. The performance of optical detectors can also degrade. Changes in either the energy emission from a light source component or sensitivity of optical detectors can result in inaccurate test data being reported by the measurement system. Further sources of inaccurate data measurements may include misuse of the measurement system instrument (for example, slamming the door of the instrument enclosure). Mishandling of the measurement system can cause misalignment of a test vial in an optical interrogation path during sample testing. Additionally, inconsistencies in chemical components of the sensor within the test vial can also result in incorrect test data being reported by the measurement system.

Embodiments of the disclosed technology solve or mitigate these and other drawbacks in optical blood culture measurement systems. Implementations of the disclosed technology can address the above-described sources of variability in components of optical blood culture measurement systems. In one implementation, the component is present inside a blood culture vial received in the optical blood culture measurement system. For example, implementations of the disclosed technology can address or mitigate variability in fluorescent sensors in blood culture vials received in the optical blood culture measurement system for testing. In another implementation, the component is equipment in the system that measures signals emitted from blood culture vials received in the optical blood culture measurement system. For example, implementations of the disclosed technology can address or mitigate variability in the equipment that measures fluorescence signals emitted by the sensors in the optical blood culture measurement system.

Embodiments of the disclosed technology are described herein with reference to optical blood culture measurement systems, such as but not limited to the BD BACTEC™ blood culture system by Becton, Dickinson and Company. It will be understood, however, that embodiments of the disclosed technology are not limited to blood culture measurement systems, and can be applied to other types of optical detection systems that rely on sensors or other materials that have a non-varying characteristic suitable for use as a reference signal for normalization of detector readings, such as an isosbestic point. For example, embodiments of the presently-disclosed technology can be implemented in immunoassays.

SUMMARY

Aspects of the present disclosure include systems and methods for normalizing fluorescence signals in an optical blood culture measurement system configured to detect the presence of an analyte of interest in a blood sample.

In one embodiment, a method of determining the presence of an analyte of interest in a blood sample under test is provided. The method includes inoculating a blood culture test vial including a sensor with the blood sample, transmitting light at an excitation frequency of the sensor to the test vial, measuring an intensity of a plurality of fluorescence signals emitted from the test vial, and normalizing the plurality of measured fluorescence signals by a reference signal that is not dependent on a measured intensity of a fluorescence signal emitted from the test vial that was inoculated with the blood sample under test.

In another embodiment, a system for determining the presence of an analyte of interest in a blood sample under test is provided. The system includes a blood culture test vial configured to receive a blood sample and comprising a sensor, a light source configured to transmit light at an excitation frequency of the sensor to the test vial, one or more detectors configured to measure an intensity of a plurality of fluorescence signals emitted from the test vial, and a processor configured to normalize the plurality of measured fluorescence signals by a reference signal that is not dependent on a measured intensity of a fluorescence signal emitted from the test vial.

In a further embodiment, a method of determining the presence of an analyte of interest in a blood sample is provided. The method includes introducing a first reference fluid into a first reference vial comprising a sensor, the first reference fluid exposing the sensor in the first reference vial to a first performance boundary condition. The method also includes transmitting light at an excitation frequency of the sensor to the first reference vial. The method further includes measuring an intensity of a plurality of fluorescence signals emitted from the sensor performing at the first performance boundary condition to generate a first reference ratio. The method includes inoculating a blood culture test vial comprising the sensor with the blood sample; transmitting light at an excitation frequency of the sensor to the test vial; and measuring an intensity of a plurality of fluorescence signals emitted from the test vial. The method also includes normalizing the plurality of measured fluorescence signals emitted from the test vial using the first reference ratio.

In still a further embodiment, a system for determining the presence of an analyte of interest in a blood sample is provided. The system includes a first reference vial including a sensor and a first reference fluid configured to expose the sensor to a first performance boundary condition. The system also includes a blood culture test vial including the sensor and configured to receive the blood sample. The system also includes a light source configured to transmit light at an excitation frequency of the sensor to the first reference vial and the test vial. The system includes one or more detectors configured to measure an intensity of a plurality of fluorescence signals emitted from the first reference vial and the test vial. The system also includes a processor configured to normalize the plurality of measured fluorescence signals emitted from the test vial using a first reference ratio generated from the measured intensities of the plurality of fluorescence signals emitted from the first reference vial.

DETAILED DESCRIPTION

Figure 1:
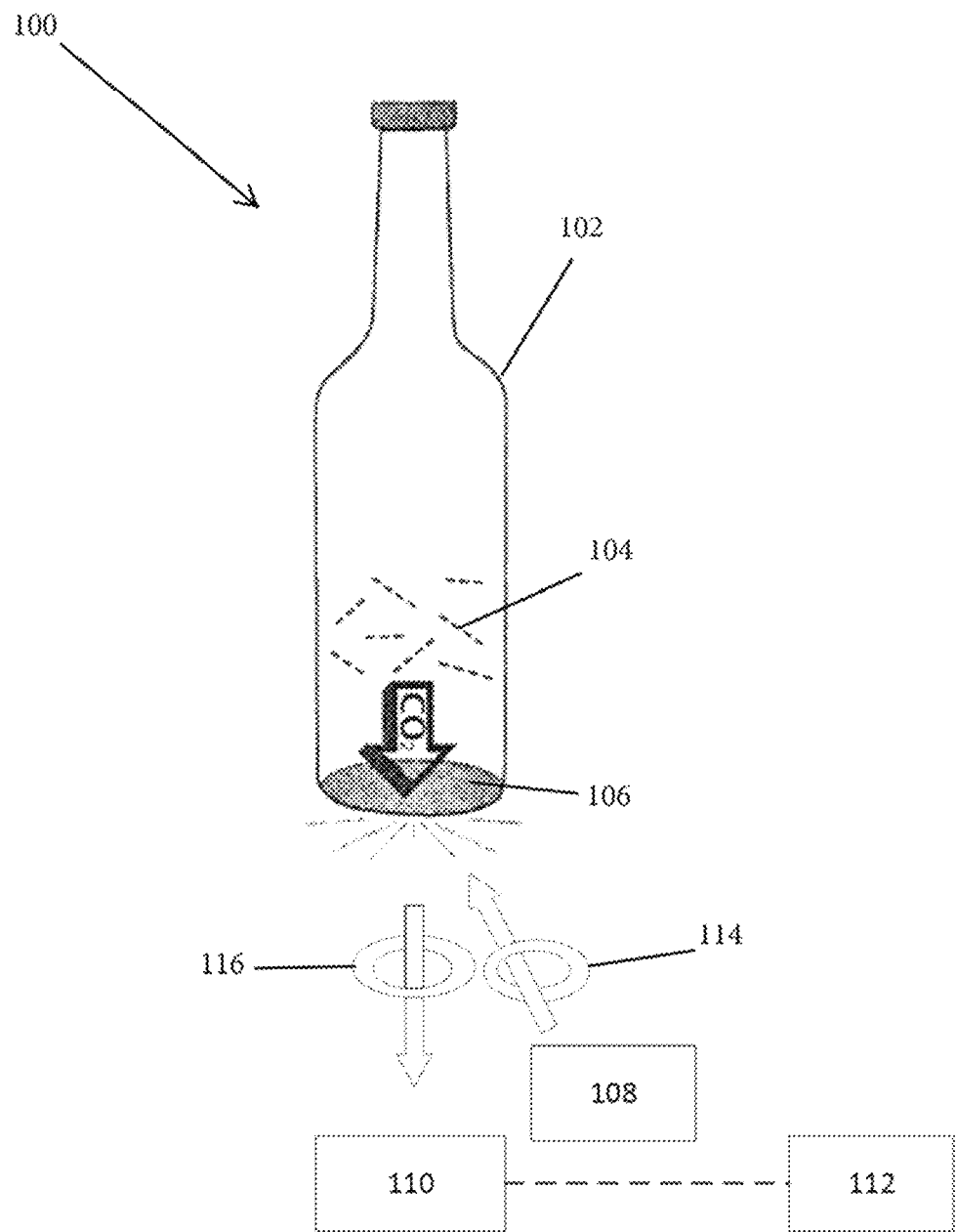
FIG. 1 depicts a schematic view of a sample measurement system in accordance with an illustrative embodiment of the present disclosure.

Any feature or combination of features described herein are included within the scope of the present disclosure provided that the features included in any such combination are not mutually inconsistent as will be apparent from the context, this description, and the knowledge of one skilled in the art. In addition, any feature or combination of features may be specifically excluded from any embodiment of the present disclosure. For purposes of summarizing the present disclosure, certain aspects, advantages, and novel features of the present disclosure are described herein. Of course, it is to be understood that not necessarily all such aspects, advantages, or features will be present in any particular embodiment of the present disclosure.

It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the present disclosure.

Embodiments described herein relate to systems and methods for optimizing detection of optical signals indicating the presence of an analyte of interest in a sample, such as a blood sample. In certain embodiments, the presence of an analyte of interest, such as a bacteria or other microorganism, is determined based on detection of a change in optical properties, such as fluorescence, correlated to growth of the analyte within the sample. For example, the sample may be introduced into a vial or other container housing a fluorescent material and an indicator material including one or more dyes that undergoes an optically-measureable change (e.g., color intensity) in response to growth of the analyte within vial. The indicator material can be configured to change optically in response to a change in a condition in the vial or a characteristic of the sample, such as but not limited to a pH indicator that undergoes an optically-measurable change (such as a change in color) in response to a change in a pH condition in the vial. The optical change of the indicator material can change the fluorescence behavior of the fluorescent material, for example, by modulating excitation of the fluorescent material and/or emission of a fluorescent signal. In certain embodiments, the fluorescent material and indicator material can be part of a sensor within the test vial.

One or more detectors can detect an intensity of the fluorescent signals emitted by the fluorescent material within the vial. The data detected by the detectors can be processed to indirectly determine a change in the amount of the analyte of interest by determining a change in the intensity of the fluorescent signals emitted by the fluorescent material.

Embodiments of the systems and methods described herein can account for or mitigate variability in components of optical blood culture measurement systems. Implementations of the disclosed technology can address the above-described sources of variability in components of optical blood culture measurement systems. In one implementation, the component is present inside a blood culture vial present in the optical blood culture measurement system. For example, embodiments of the disclosed technology can address or mitigate variability in fluorescent sensors in blood culture vials received in the optical blood culture measurement system for testing. Embodiments of the systems and methods described with reference to this implementation normalize detector readings using a reference signal that does not change as a function of the performance characteristics of the measurement system itself. Advantageously, reference signals according to the present disclosure can be based on a non-varying characteristic of a component present in the measurement system, such as a non-varying characteristic of the sensor in the test vial. In some cases, a reference signal according to the present disclosure is not dependent on a measured intensity of a fluorescence signal emitted from a test vial inoculated with a test sample. For example, the reference signal may not vary with or be related to measurements of fluorescence signals emitted from the test vial. In one non-limiting example described below, the reference signal is an isosbestic point of a component of a sensor present in the test vial. The component can be a fluorescent material or an indicator material of the sensor.

Other implementations of the present disclosure address or mitigate variability introduced by hardware in the system that measures signals emitted from blood culture vials. For example, implementations of the disclosed technology can address or mitigate variability in an excitation light, an excitation filter, an emission filter, a photodiode, or any combination of these components, that form part of the system that measures fluorescence signals emitted by the sensors in the optical blood culture measurement system. As will be described below with reference to FIGS. 5-6, a measurement system measures fluorescence signals from one or more reference vials performing in extreme (for example, high and low pH) conditions expected to occur in a test vial. These measurements are used to develop one or more performance boundary conditions for test vials received in the measurement system. The measurement system measures fluorescence signals emitted from test vials inoculated with samples under test. These test vial fluorescence signals can be compared to the one or more performance boundary conditions to address or mitigate variability in hardware components of the measurement system.

Embodiments of the present disclosure are described with reference to normalizing fluorescence signals emitted by a test vial to address variability in components of optical blood culture measurement systems. It will be understood that methods of adjusting, dividing, and comparing fluorescence signals using reference signals and reference ratios described herein can also be described as calibrating the fluorescence signals.

Implementations of the Present Disclosure Using a Reference Signal to Normalize Variability in Sensor Readings Due to Variability in Components Present in a Test Vial Implementations of the present disclosure that use a reference signal to normalize variability in sensor readings due to variability in components present in a test vial will now be described with reference to FIGS. 1 through 4. The reference signal does not change as a function of the performance characteristics of the measurement system itself, and can be used to normalize fluorescence signals emitted from a test vial inoculated with a sample under test. Although the following examples are described with reference to an isosbestic point of a component present in the test vial, such as a fluorescent material or an indicator material, it will be understood that the present disclosure can be applied to other reference signals that do not vary with nor rely on fluorescence signals measured from the test vial inoculated with a sample under test.

FIG. 1 shows a schematic view of a measurement system 100 in accordance with an illustrative embodiment of the present disclosure. The measurement system 100 includes a test vial 102, a light source 108, and a detector 110.

The test vial 102 is configured to receive a sample 104, such as a blood sample. The measurement system 100 is configured to determine the presence or absence of an analyte of interest in the sample 104 received in the test vial 102. The analyte of interest can be, for example, a microorganism or bacteria. The test vial 102 can further house a sensor 106 including a fluorescent material and an indicator material. The vial 102 may also house liquid media, which may support the growth of microorganisms within the vial 102. The test vial 102 can be, for example, a blood culture bottle.

The light source 108 can be activated to emit light at one or more wavelengths or ranges of wavelengths to excite the fluorescent material of the sensor 106. In certain embodiments, the light source 108 can include one or more light-emitting diodes (LEDs).

The detector 110 can be configured to detect fluorescence emitted by the fluorescent material of the sensor 106 following excitation thereof. The detector 110 can be a silicon photodiode, a PIN silicon diode, a GaAsP photodiode or any other suitable photodetector. In some embodiments, the detector 110 can include a photovoltaic device, a photoresistive device, a photoconductive device, or any other suitable device for detecting a signal emitted from the sensor 106. In certain embodiments, a plurality of detectors 110 may be employed for measuring fluorescence signals emitted by the sensor 106.

The system 100 may include one or more excitation filters 114 configured to filter light from the light source 108 to provide only light of a particular wavelength or range of wavelengths to the fluorescent material. For example, in certain embodiments, one or more excitation filters 114 may filter light to provide a particular wavelength or range of wavelengths to the fluorescent material that correspond to an absorption spectrum of the fluorescent material.

The system 100 may include one or more emission filters 116 configured to filter light to provide a wavelength or range of wavelengths to the detector 110. For example, in certain embodiments, one or more emission filters 116 may filter light to provide a wavelength or range of wavelengths to the detector 110 that correspond to an emission spectrum of the fluorescent material.

The fluorescent material used in the system 100 may be selected based on the emission spectrum of the light source 108 and/or the specifications of the detector 110. In certain embodiments, the fluorescent material can include one or more fluorophores. Examples of fluorophores that may be suitable for use with the embodiments described herein include, but are not limited to, Thionin, Naphtho fluorescein, Carboxynaptho fluorescein, 3, 3'-dimethyloxadicarbocyanine, Sulforhodamine B, Pyronine B, Rhodamine B, Nile red phenoxazon 9, Evans blue, Rhodamine 6G perchlorate, Sulforhodamine G, 7-aminoactinomycon D, EOSIN, Rhodamine 110, and Rhodamine 123.

As described herein, the indicator material within the sensor 106 may undergo an optical change in response to a change in an analyte of interest within the sample, for example a change in the concentration of the analyte within the sample. In certain embodiments, an indicator material is selected that undergoes changes in optical properties based on changes in the concentration of one or more of $CO_2$, $O_2$, $H_2S$, $NH_3$, or any other suitable compound known in the art, present in the test vial. In certain embodiments, an indicator is selected that undergoes changes in optical properties based on changes in pH in the test vial due to changes in concentration of the analyte in the sample.

In certain embodiments, the indicator material can include a pH indicator. Examples of pH indicators that may be suitable for use with the embodiments described herein include, but are not limited to, Propyl Red, P-nitrophenol, Azolitmin, Chlorophenol red, 3,6-dihydroxy xanthone, Alizarin, Bromxylenol blue, M-dinitrobenzoyleneurea, Bromthymol blue, Aurin (Aosolic acid), Neutral red, Cresol red, Bromocresol red, Bromocresol purple, Resolic acid, Nile Blue, Phenol red, Nitramine, Cresol purple, and Methyl yellow.

The optical change in the indicator material can act as an optical filter to change the amount of light exciting the fluorescent material or emitted from the fluorescent material of the sensor 106. Accordingly, a change in the concentration of the analyte of interest within the sample can cause a change in the fluorescent signal detected by the detector 110 by changing the optical properties of the indicator material of the sensor 106. Consequently, changes in the intensity of the fluorescent signals detected by the detector 110 may be indicative of a change in the concentration of the analyte of interest within the sample.

As an example, in certain embodiments, the system 100 is configured to detect the presence of bacteria or microorganisms within a sample placed within the vial 102. In embodiments in which bacteria is the analyte of interest, the indicator may be a pH indicator, which is configured to undergo a change in absorbance as the pH changes. When bacteria grow, $CO_2$ is respired. $CO_2$ can mix with aqueous media within the vial 102 to produce carbonic acid. Increased amounts of carbonic acid result in a decrease in pH. The absorbance of the pH indicator is reduced as the pH within the vial 102 decreases, which allows for more excitation energy to reach the fluorescent material within the sensor 106, resulting in an increase in the intensity of fluorescent emission from the fluorescent material. As described herein, the fluorescent material can include one or more fluorophores. The detector 110 can detect the increased fluorescent emission intensity, which may act as an indirect measurement of an increase in $CO_2$ concentration. As described above, $CO_2$ concentration is directly correlated with bacterial growth. Accordingly, detection of an increased fluorescent intensity by the detector 110 may indicate the presence of bacteria within the sample.

In certain embodiments, the measurement system 100 may further include a processor 112 configured to perform signal processing to determine presence of the analyte based on changes in measured fluorescence intensity by the detector 110. In certain embodiments, the processor may be part of a computing system. Such a computing system may also include one or more of a memory, an input, and a display. The memory, which can include read-only memory (ROM) or both ROM and random access memory (RAM), can be configured to provide instructions and data to the processor 112. For example, the memory can store one or more modules that store data values defining instructions to configure processor 112 to perform signal processing functions.

In certain embodiments, the fluorescence signals detected by the one or more detectors may be normalized by the processor 112 using a reference signal. In certain embodiments, the measurement system normalizes detector readings using a reference signal that does not change as a function of the performance characteristics of the measurement system itself. For example, a reference signal can be selected that is based on a non-varying characteristic of a component present in the measurement system, such as a non-varying characteristic of the sensor in the test vial. In one non-limiting example of the present disclosure, a reference signal is selected that is not dependent on a measured intensity of a fluorescence signal emitted from the test vial inoculated with a test sample. For example, the reference signal may not vary with or be related to measurements of fluorescence signals emitted from the test vial. In non-limiting examples described with reference to FIGS. 2-4 below, the reference signal is an isosbestic point of a component of a sensor present in the test vial.

An isosbestic point can be generally defined as a wavelength, wavenumber, or frequency at which a total absorbance of a sample does not change during a chemical reaction or a physical change of the sample. An isosbestic point of a component present in the measurement system can be used as a reference signal to normalize detector readings. In one non-limiting example described in detail with reference to FIGS. 2 and 3 below, an isosbestic point of the fluorescent material of the sensor 106 may be determined and used to generate a reference signal. For a fluorescent material, an isosbestic point may be defined as a specific wavelength where the absorption spectrum of the fluorescent material crosses the emission spectrum of the fluorescent material. In another non-limiting example described in detail with reference to FIG. 4 below, an isosbestic point of the indicator material of the sensor 106 may be determined and used to generate a reference signal. In cases where the indicator material is a pH indicator, an isosbestic point may be defined as a specific wavelength where the absorption spectra of the pH indicator at various pH conditions cross. The isosbestic point of the component (for example, the fluorescent material or the pH indicator) is an inherent property of the material. As a result, using the isosbestic point as a reference signal according to the present disclosure does not rely on or change with the performance characteristics of the measurement system. Advantageously, the isosbestic point of a component present in the measurement system can enable real time, continuous normalization of blood culture readings detected by the measurement system. Examples of such isosbestic points will now be described with reference to an isosbestic point 205 illustrated in FIG. 2 and an isosbestic point 305 illustrated in FIG. 3.

Figure 2:
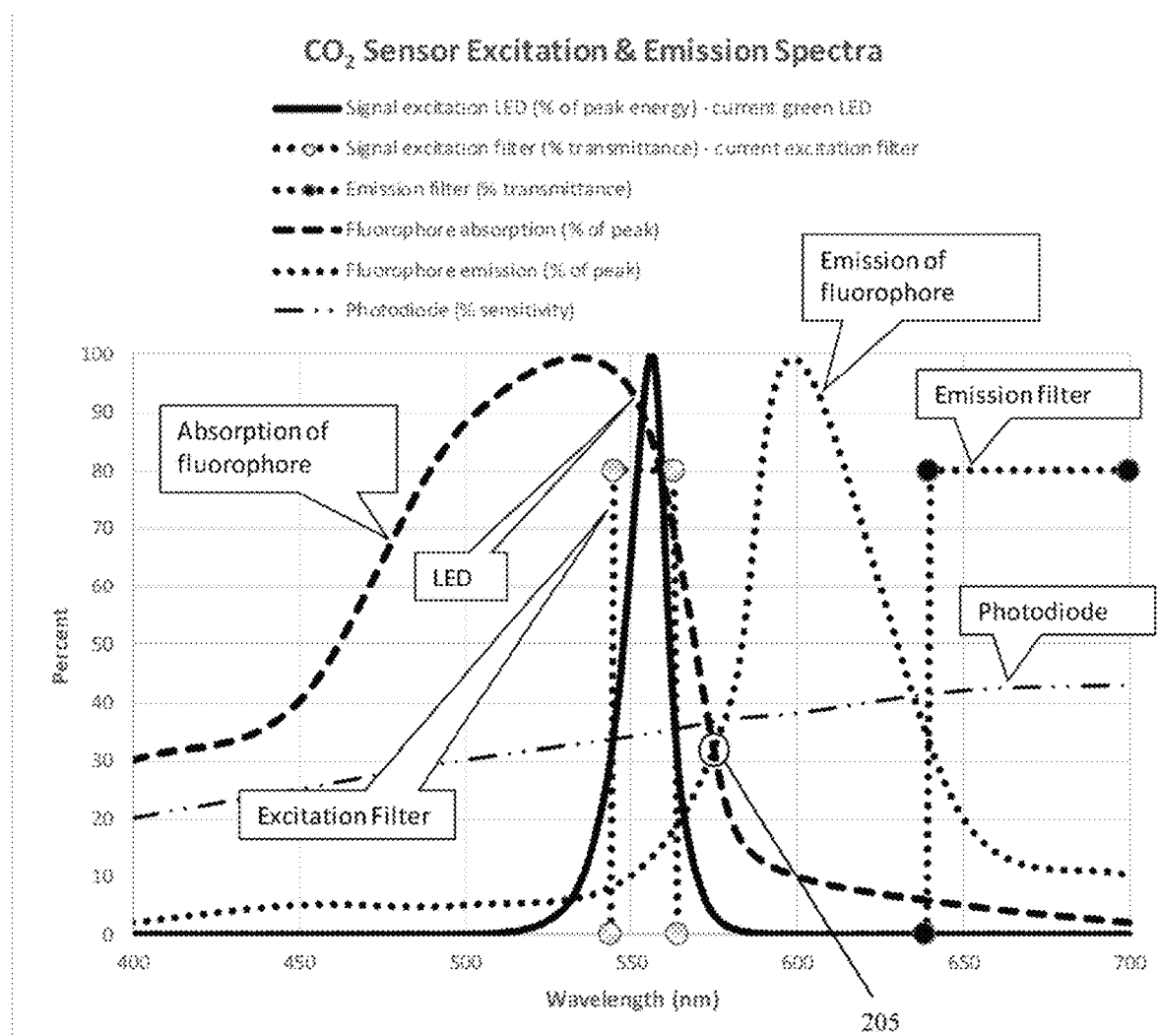
FIG. 2 depicts a graph showing the spectra of various optical components of a sample measurement system and the absorption and emission spectra of a sensor including a fluorescent material in accordance with an illustrative embodiment of the present disclosure.

FIG. 2 shows a graph depicting an example of spectra of optical components that may be used in a measurement system such as measurement system 100 including an LED light source, a photodiode detector, an excitation filter, and an emission filter. FIG. 2 also shows an absorption spectra of a rhodamine-based fluorophore and an emission spectra of the rhodamine-based fluorophore of a sensor 106 configured to detect a $CO_2$ condition in the test vial. As shown in FIG. 2, an isosbestic point 205 occurs where the absorption spectrum of the fluorophore and the emission spectrum of the fluorophore cross. In this example, the isosbestic point is about 550 nm.

Figure 3:
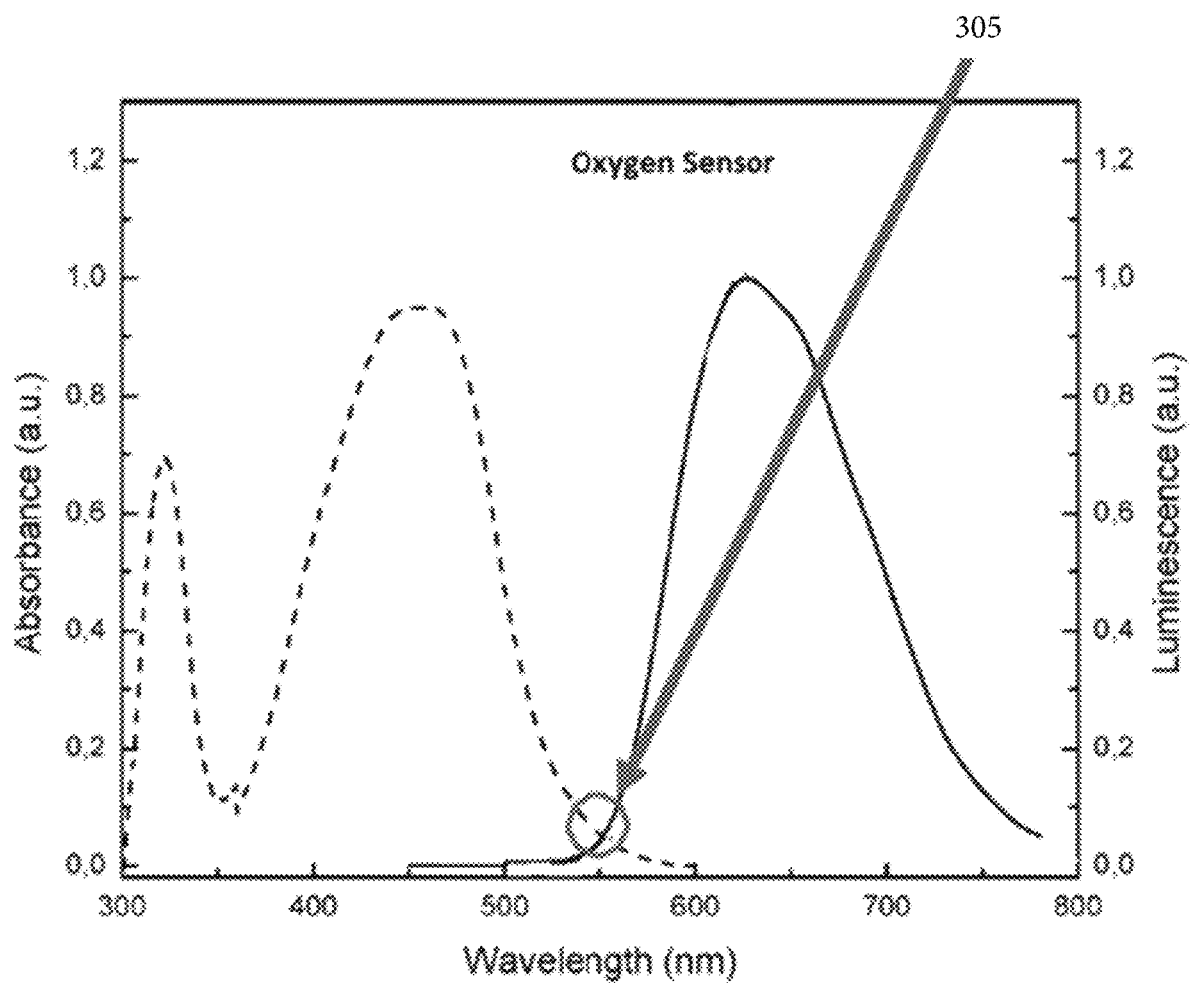
FIG. 3 depicts a graph showing the absorption and emission spectra of a sensor including a fluorescent material in accordance with an illustrative embodiment of the present disclosure.

FIG. 3 shows a graph depicting absorption spectra and emission spectra of an oxygen sensor that may be used in a measurement system such as measurement system 100. Examples of oxygen sensors are described in U.S. Pat. No. 6,080,574. As shown in FIG. 3, an isosbestic point 305 occurs where the absorption spectrum of the oxygen sensor and the emission spectrum of the oxygen sensor cross. In this example, the isosbestic point is about 550 nm. It will be understood that the presence of an isosbestic point is not limited to only $CO_2$ sensors or oxygen sensors described in the examples implementations of FIGS. 2 and 3, and that using an isosbestic point as a reference signal according to the present disclosure may be generally applicable to a variety of analyte sensors including sensors for $H_2S$, $NH_3$, or any other suitable compound known in the art.

In another embodiment, an isosbestic point for an indicator material of a sensor may be used to generate a reference signal for normalization of detector readings. In cases where the indicator material is a pH indicator, an isosbestic point may be defined as a point in the absorption spectrum (i.e., specific wavelength) at which the absorption curves of the pH indicator at various pH states cross.

Figure 4:
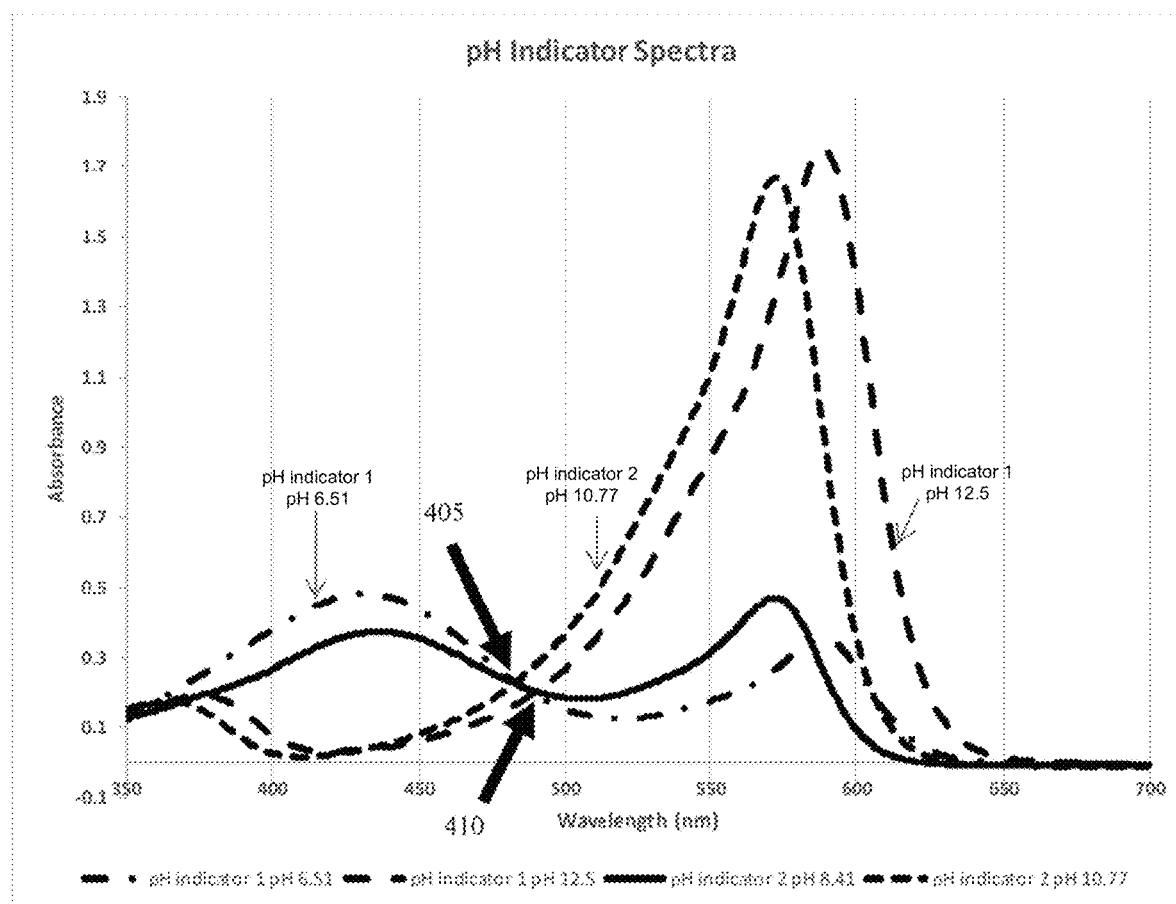
FIG. 4 depicts graph showing the absorption spectra of pH indicators at various pH states in accordance with an illustrative embodiment of the present disclosure.

Examples of such isosbestic points are shown at isosbestic points 405 and 410 in FIG. 4. FIG. 4 shows a graph depicting absorption spectra for a first pH indicator, labeled "pH indicator 1", and a second pH indicator, labeled "pH indicator 2", at various pH states. FIG. 4 depicts an absorption spectrum for pH indicator 2 at a pH of 8.41, and an absorption spectrum for pH indicator 2 at a pH of 10.77. As shown in FIG. 4, the absorption spectra for pH indicator 2 at pHs of 8.41 and 10.77 overlap at isosbestic point 405. In this non-limiting example, the isosbestic point 405 is about 484 nm. FIG. 4 also depicts an absorption spectrum for pH indicator 1 at a pH of 6.51, and an absorption spectrum for pH indicator 1 at a pH of 12.5. As shown in FIG. 4, the absorption spectra for pH indicator 1 at pHs 6.51 and 12.5 overlap at isosbestic point 410. In this non-limiting example, the isosbestic point 410 is about 489 nm. It will be understood that the isosbestic point of a pH indicator such as pH indicator 1 and pH indicator 2 is dependent on the concentration of the pH indicator in the sensor. The particular isosbestic point of a pH indicator provided at a particular concentration in a sensor of the test vial can be determined empirically or using any other suitable method.

Implementations of the Present Disclosure Using Reference Ratios to Normalize Variability in Sensor Readings Due to Variability in Hardware Components of a Measurement System Implementations of the present disclosure that use reference ratios to normalize variability in sensor readings due to variability in hardware components of a measurement system will now be described with reference to FIGS. 5 and 6. The reference ratios change as a function of the performance characteristics of the measurement system, and can be used to normalize fluorescence signals emitted from a test vial inoculated with a sample under test and measured using the same measurement system. Although the following examples are described with reference to certain hardware components of the measurement system, such as an excitation light, an excitation filter, an emission filter, and a photodiode, it will be understood that the present disclosure can be applied to any of these components singly or in combination, as well as to other hardware components of an optical blood culture measurement system.

In a non-limiting embodiment described with reference to FIGS. 5 and 6 below, a ratio of pH indicator absorbances at two specified wavelengths provides a relative measurement that can be used as a reference ratio to normalize or calibrate detector readings from a test vial. In a first non-limiting implementation, detector readings are normalized using two reference ratios. In a second non-limiting implementation, detector readings are normalized using a single reference ratio.

In implementations that use two reference ratios to normalize detector readings, a two-point normalization process is performed using two reference vials that are set up to expose the pH indicator in the vials to two extreme states that can be expected to exist in a test vial during measurement of an actual test specimen. Fluorescence signals from the two reference vials are measured using a measurement system that includes emission filters having selected criteria, where the selected criteria are based on the expected absorbance characteristics of the pH indicators performing under extreme conditions in the two reference vials. In this example, the extreme conditions are a low pH condition and a high pH condition. A ratio of the fluorescence signals measured from each reference vial with the two emission filters is proportional to the pH of the media in each reference vial, and can be used as reference ratios to normalize the ratio of detector readings taken during a blood culture test of a test vial employing the same pH indicator.

Figure 5:
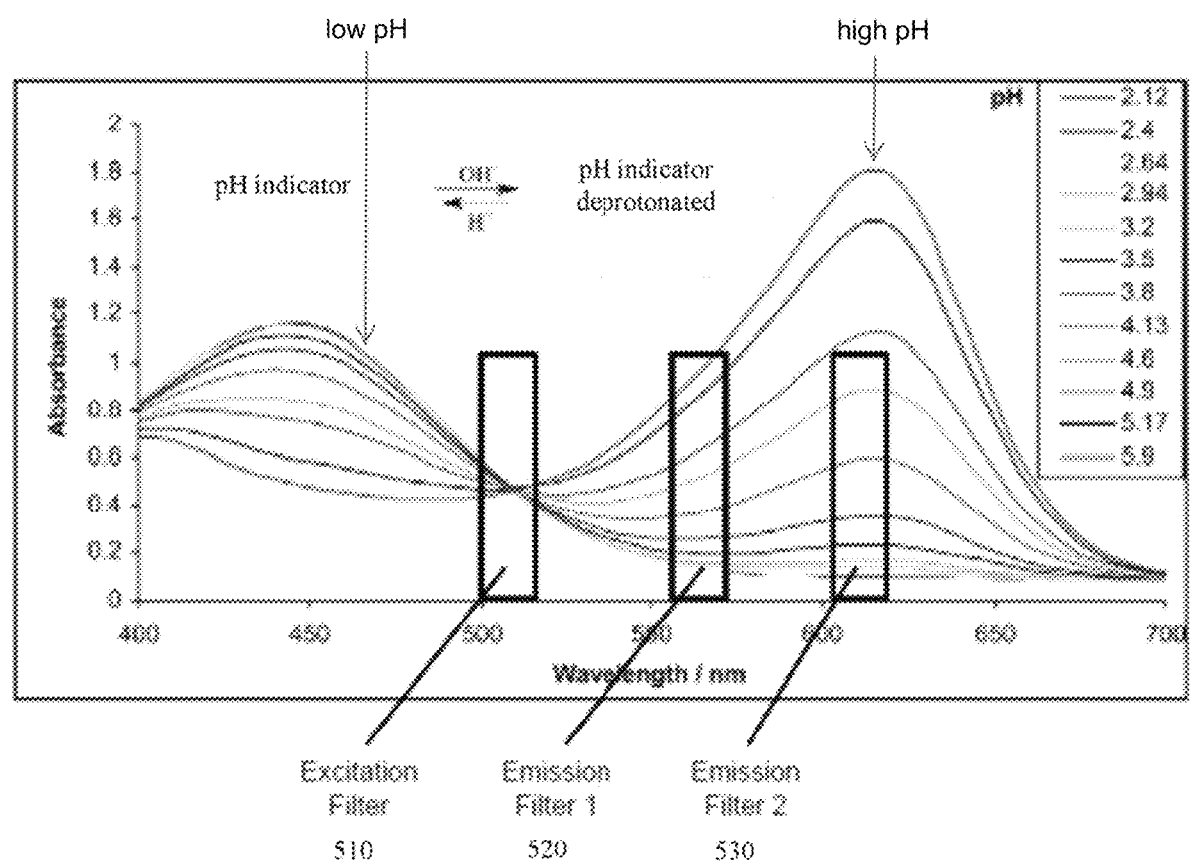
FIG. 5 depicts a graph showing the absorption spectra of a pH indicator at various pH states in accordance with an illustrative embodiment of the present disclosure.

FIG. 5 shows a graph depicting absorption spectra for an indicator material, in this case a pH indicator, at various pH states. FIG. 6 shows a flowchart depicting a process 600 for determining a signal based on the ratio of pH indicator absorbances at two specified wavelengths using a measurement system similar to the measurement system 100 described with respect to FIG. 1. The measurement system in this implementation includes excitation and emission filters with specific selected criteria.

The process of normalizing or calibrating the measurement system includes two reference vials, each vial including a sensor containing a pH indicator and a fluorophore. The sensors in the two reference vials are exposed to extreme conditions expected to exist during test specimen evaluation in the actual test specimen vials. The extreme conditions in this non-limiting example are a high pH condition and a low pH condition.

The process 600 of obtaining the reading for a single vial of the two reference vials begins at a step 610, wherein a light source, such as an LED, is activated to emit light over a range of wavelengths to excite the fluorophore. At a step 620, an excitation filter filters the light emitted by the LED light source. The excitation filter can be selected so that a filter window 510 defined by the excitation filter encompasses or is near the isosbestic point of the pH indicator absorbance spectrum. In this non-limiting example, the isosbestic point of the pH indicator is about 505 nm. After the excitation filter filters the light emitted by the LED light source, the pH indicator absorbs at least some of the light emitted by the LED light source at a step 630. After the pH indicator absorbs at least some of the light emitted by the LED light source, a fluorophore in the sensor absorbs at least some of the light emitted by the LED light source, and in response, emits a fluorescent signal at step 640. The fluorescent signal emitted by the fluorophore is then filtered by a first emission filter at a step 650a. The same fluorescent signal emitted by the fluorophore is filtered by a second emission filter at a step 650b.

In certain embodiments, the first emission filter may be a narrow band pass filter having a filter window 520 that encompasses or is substantially close to a low end of the fluorescence output spectrum of the fluorophore. For example, the filter window 520 may encompass or be substantially close to 575 nm. The second emission filter may be a narrow band pass filter having a filter window 530 that encompasses or is substantially close to an absorbance peak of the pH indicator. For example, the filter window 530 may encompass or be substantially close to 620 nm. Accordingly, the signal change measured with the first emission filter as the pH of the sensor changes between the expected extremes of pH will be less than the change of signal measured with the second emission filter. The ratio of the two signals will be proportional to the pH of the indicator.

After the fluorescence signal emitted from the fluorophore is filtered by the first emission filter, the resulting signals are detected by a first photodiode at step 660a. The same fluorescence signal emitted from the fluorophore is filtered by the second emission filter, and the resulting signals are detected by a second photodiode at step 660b. Each of the first and second photodiodes can then produce an electronic signal proportional to detected light intensity at steps 670a and 670b. At step 680, a ratio comparing the signal proportional to detected light intensity at the first photodiode and the signal proportional to the detected light intensity at the second photodiode is generated. This ratio has been found to be proportional to the pH of the media. This ratio also indicates an average slope of absorbance spectra for the pH indicator between 575 nm to 620 nm.

The process 600 can be performed for two reference vials, a low-pH limit reference vial and a high-pH limit reference vial. For example, the sensor in the low-pH limit reference vial is exposed to an extremely low pH condition at the lower boundary of pH conditions to which a sensor in a test vial is expected to be exposed during test events. The ratio generated by the low-pH limit reference vial represents a low-level ratio. The sensor in the high-pH limit reference vial is exposed to an extremely high pH condition at the upper boundary of pH conditions to which a sensor in a test vial is expected to be exposed during test events. The ratio generated by the high-pH limit reference vial represents a high-level ratio. The low-level ratio and the high-level ratio represent two performance boundary conditions (a low pH condition and a high pH condition) within which test vials can be expected to perform. The low-level ratio and the high-level ratio can also represent the outer boundaries of a range or continuum of performance characteristics of hardware components of the measurement system.

These two performance boundary conditions, and the range of performance characteristics they represent, can be used to normalize readings from a test vial received in the same measurement system. The process 600 can be repeated on a test vial after it has been inoculated with a test sample. As explained above, in step 680, a ratio comparing the signal proportional to detected light intensity at the first photodiode and the signal proportional to the detected light intensity at the second photodiode is generated for the test vial. This test vial ratio may be compared to the reference ratios measured from the reference vials to normalize detector readings in accordance with the embodiments of the present disclosure. The ratio, of the fluorescent signal measured by the first emission filter to the fluorescent signal measured by the second emission filter, can also be compared to the ratios obtained from the reference vials to determine the pH state of the sensor. In one non-limiting example, the relative position of the test vial ratio within a range of ratios bounded by the low-level ratio and the high-level ratio can be used to normalize or calibrate fluorescence measurements of the test vial. The relative position of the test vial ratio within the range of ratios established by the reference vials can be used to assess variability in hardware components of the measurement system at the time signals from the test vial are being measured, in some cases in real time. In another non-limiting example, a measured test vial ratio that is outside the range of ratios established by the reference vials can indicate that a hardware component of the measurement system is inoperative, malfunctioning, or is otherwise not performing as expected.

Implementations of the present disclosure can use a single reference ratio to normalize variability in sensor readings due to variability in hardware components of the measurement system. In this case, the process of normalizing or calibrating the measurement system includes one reference vial containing a sensor containing a pH indicator and a fluorophore. The sensor is exposed to an extreme condition expected to exist during test specimen evaluation in the actual test specimen vials. The extreme condition in this non-limiting example can be a high pH condition or a low pH condition. Measurements are taken and a single reference ratio is generated in accordance with the method 600 described above. The process 600 is repeated to obtain measurements of and generate a test vial ratio for a test vial inoculated with a sample under test. The single reference ratio can be used to assess variability in hardware components of the measurement system at the time signals from the test vial are being measured, in some cases in real time. In one example, the difference between the reference ratio and the test vial ratio is calculated to give an indication of the performance characteristics of the hardware components of the measurement system. In another example, a test vial ratio that is greater than or less than the reference ratio (depending on whether the reference ratio represents a low pH condition and a high pH condition) can indicate that a hardware component of the measurement system is inoperative, malfunctioning, or is otherwise not performing as expected.

It will be understood that determination of a ratio as described with reference to FIG. 6 may be subject to several variables including relative sensitivities of the photodiodes, optical coupling of the photodiodes, and accuracy of the emission filters, taken singly or in combination. In certain embodiments, the process of FIG. 6 can be repeated using various conditions in reference vials that may be expected to exist in a bottle during sample measurement. The reference ratios in this example do not depend on a measured intensity of a fluorescence signal emitted from a test vial containing the specimen under test. It will also be understood that implementations for normalizing fluorescence signals from a test vial using one or more reference ratios can be performed in conjunction with normalization of fluorescence signals using a reference signal described above with reference to FIGS. 2-4.

Figure 6:
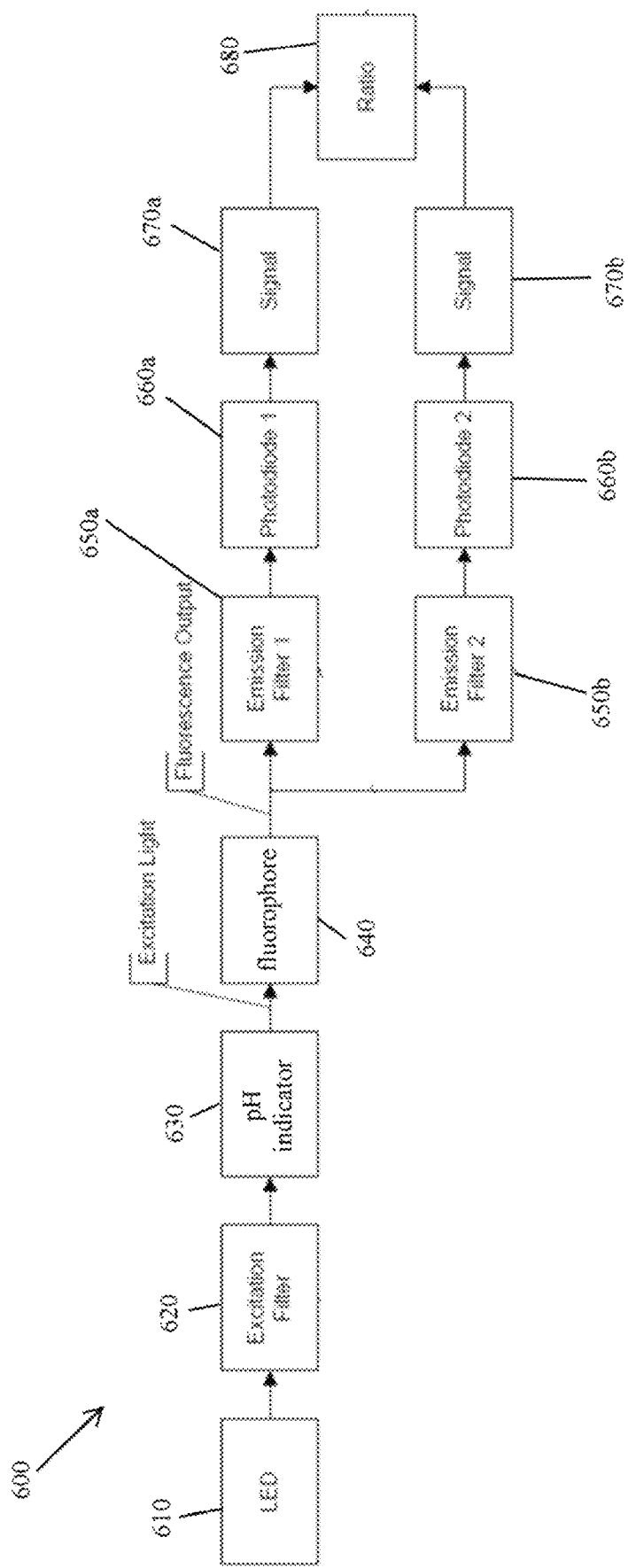
FIG. 6 depicts a flowchart showing a process for normalizing variability in components that measure fluorescence signals in an optical blood culture measurement system in accordance with an illustrative embodiment of the present disclosure.

As described herein, a reference signal that is not dependent on a measured intensity of a fluorescence signal emitted from the test vial, such as the isosbestic point reference signals described with respect to FIGS. 2-4 and the one or more reference ratio described with respect to FIGS. 5 and 6, may be used to normalize fluorescence signals detected by a detector of a measurement system, such as detector 110. Such reference signals and reference ratios may vary based on a concentration of fluorescent material within a vial or for different vial characteristics. It will be understood, however, that the reference signals and reference ratios according to embodiments of the present disclosure, are constant or substantially constant for a particular amount of fluorophore and a particular bottle design. Accordingly, a reference signal as described herein with respect to FIGS. 2-4 and one or more reference ratios as described herein with reference to FIGS. 5 and 6 may be used for normalizing data from multiple test vials having the same vial design and amount or concentration of fluorophore in the sensor. In certain embodiments, a single reference signal may be used for a plurality of test vials. Similarly, a single low-level ratio and a single high-level ratio may be used to normalize fluorescence signals from a plurality of test vials. Alternatively, in other embodiments, a new reference signal may be determined for each test vial and/or a new low-level ratio and a new high-level ratio may be determined for each test vial. Reference signals may be determined empirically. In other embodiments, known reference signals are used, for example, from a database. As an example, the isosbestic point may be known for a particular fluorophore. As another example, the isosbestic point may be known for a particular fluorophore manufactured by a particular source. A reference signal based on the isosbestic point, amount of fluorophore, and/or bottle optical characteristics of a lot or batch of blood culture test vials may also be determined at the manufacturer and transmitted to the user of a blood culture measurement system via indicia provided on or with the blood culture test vials.

Example Method for Determining Presence of an Analyte in a Blood Sample

Figure 7:
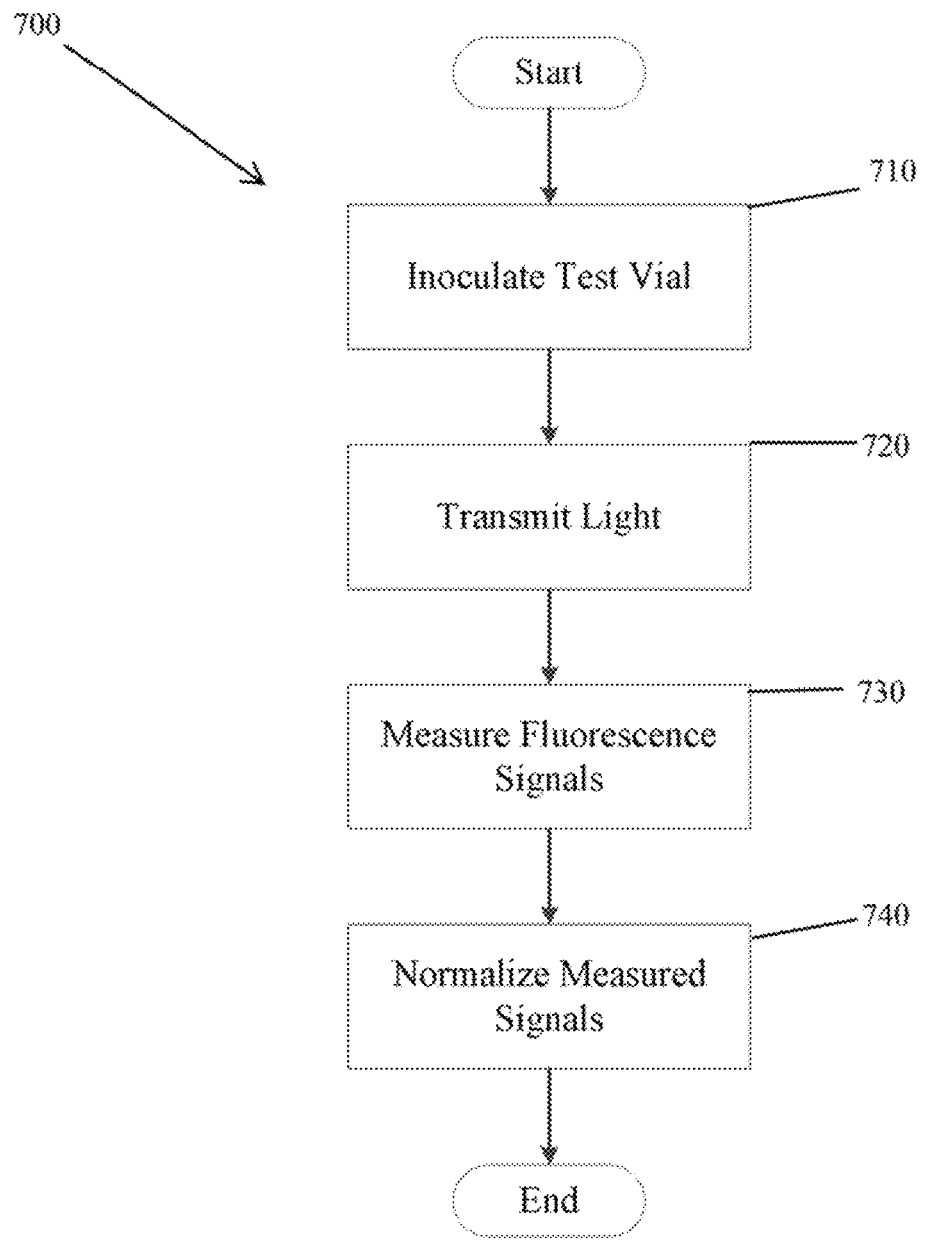
FIG. 7 depicts a flowchart showing a process for optimizing detection of optical signals indicating the presence of an analyte of interest in a blood sample in accordance with an illustrative embodiment of the present disclosure.

FIG. 7 depicts a process 700 for determining the presence of an analyte of interest in a blood sample. The process begins at a step 710, wherein a blood culture test vial having a sensor, such as vial 102 as described with respect to FIG. 1, is inoculated with a blood sample. The sensor can include a fluorescent material and an indicator, such as sensor 106 as described with reference to FIG. 1.

After the blood culture test vial is inoculated, the process 700 moves to a step 720, wherein excitation light is transmitted to the test vial at an excitation frequency of the sensor. The excitation frequency can be a frequency or range of frequencies within an absorption spectrum of the fluorescent material. The light may be transmitted by a light source, such as light source 108 as described with respect to FIG. 1.

After the light is transmitted to the test vial, the process 700 moves to a step 730, wherein an intensity of fluorescence signals emitted from the test vials is measured. As described herein, the fluorescence signals may be emitted by the fluorescent material of the sensor. The fluorescence signals can be measured by a detector, such as detector 110 as described with respect to FIG. 1. In certain embodiments, measuring the intensity of the fluorescence signals at step 730 includes filtering the plurality of fluorescence signals using a first emission filter.

After the intensity of the fluorescence signals is measured, the process 700 moves to a step 740, wherein the fluorescence signals are normalized using a reference signal that is not dependent on a measured intensity of a fluorescence signal emitted from the test vial inoculated with the test sample. In some embodiments, the reference signal can be an isosbestic point of the sensor in the test vial. In some embodiments, the reference signal can be an isosbestic point of a $CO_2$ sensor in the test vial. In some embodiments, the isosbestic point can be an isosbestic point of a fluorescent material of the sensor within the test vial, for example, as described with respect to FIGS. 2 and 3. In some embodiments, the isosbestic point can be an isosbestic point of a pH indicator of the sensor in the test vial, for example, as described with respect to FIG. 4. A reference signal according to embodiments of the present disclosure can be used to normalize fluorescence signals measured at step 740 by dividing the measured fluorescence signals by the reference signal.

In some embodiments, at step 730, fluorescence signals are normalized using one or more reference ratios that are not dependent on a measured intensity of a fluorescence signal emitted from the test vial inoculated with the test sample. The reference ratios used to normalize the fluorescence signals at step 730 can be ratios of indicator absorbances at two specified wavelengths, for example, as described herein with respect to FIGS. 5 and 6.

Although normalizing fluorescence signals to optimize detection of the presence of an analyte of interest in a blood sample is described with respect to the process 700 described in FIG. 7, one of skill in the art would understand that methods described herein are not limited to blood samples, but may be applicable to the detection of microorganisms in any medium known in the art. Further, one of skill in the art one of skill in the art would understand that methods described herein are not limited to normalizing fluorescence signals, but may be applicable to normalizing other types of optical signals to detect analytes of interest in a sample.

The use of a reference signal that is not dependent on a measured intensity of a fluorescence signal emitted from a test vial, such as the reference signals described with respect to FIGS. 2-4, can have numerous advantages over a reference signal that is dependent on an intensity of a fluorescence signal emitted from a test vial. Use of a reference signal in accordance with embodiments described herein can improve detector sensitivity by eliminating variability in an initial detector reading as a source of variability of the reported measurement system reading. Variability in an initial detector reading contributes proportionally to uncertainty in the measurement system output, which is equivalent to the resolution capability of the measurement system itself. In embodiments described herein in which use of the initial sensor reading to normalize detector readings is eliminated, the sensitivity of the detector is improved which advantageously results in a higher resolution measurement system.

Further, use of a reference signal and one or more reference ratios in accordance with the embodiments described herein can improve or eliminate error due to DVE because the output signal of the measurement system is not normalized using an initial detector reading. Use of a reference signal in accordance with the embodiments described herein also obviates the need to compensate for sensor temperature fluctuations.

Use of a reference signal in accordance with the embodiments described herein can also eliminate the need to measure and maintain a moving average of the measurement system output measurements. Embodiments of the present disclosure can provide a real-time measure of activity in the test vial and/or eliminate as much as a one hour delay required to establish a stable moving average signal in current technologies.

There are additional advantages associated with embodiments of the present disclosure. A reference signal that includes or is related to an isosbestic point of a component in the measurement system will not vary in its specific wavelength position for a given concentration of the component. This lack of variance in the reference signal makes it ideally suited to normalize detector readings of the measurement system. At the same time, a reference signal that does not vary based on a measured intensity of a fluorescence signal emitted from a test vial as described herein can serve as a real-time quality indicator for a measurement system, such as measurement system 100. Reference ratios according to the present disclosure can also serve as a real-time quality indicator for the measurement system. In implementations where the reference signal is determined with each test vial or by periodically testing reference vials, a determined reference signal or test reference ratio that is either too high or too low relative to historic or expected reference signals or reference ratios can be a real-time indicator that the measurement system is degraded or faulty. In these cases, the measurement system can be programmed to automatically disregard the measurement of an assay test vial displaying an intensity outside of a specified value range.

For example, because embodiments of the reference signals according to the present disclosure should not vary during testing of a vial sample placed in a measurement system, the reference signal can be measured during the assay vial test duration to determine errors in the measurement system. In certain embodiments, the measurement system can be configured to disregard data if the reference signal varies during the assay vial test duration. Alternatively, the measurement system may be programmed to correct or accommodate sample output signals based on detected variation in the reference signals described herein. These advantages are also applicable to use of reference ratios according to the present disclosure.

In addition, the absolute level of an isosbestic signal reading from a measurement system can be useful to determine the health of the measurement system itself. The isosbestic signal will be expected to vary only based on the amount and/or concentration of fluorophore in the sensor and the bottle optical characteristics, the expected range of which can be determined through empirical testing or other suitable methods. An isosbestic signal that is below an established threshold could indicate either a bad bottle/sensor, or a degraded and/or failing measurement system. Identification of the isosbestic signal reading that is below the established threshold can alert the operator of the measurement system to check for and remedy these conditions.

Additionally, the use of a reference signal as described herein can allow for identification of a particular test vial. By design, reference signals in accordance with the present disclosure do not change between test vials. As a result, the reference signal may act as an identification marker that can be correlated with the test vial and measured to confirm the identity thereof. This identification marker may be used as verification that a sensor-containing test vial is supplied by a specific manufacturer. The identification marker may also serve as an indication that a competitor has copied a test vial sensor chemistry. For example, a reference signal at an isosbestic point may be determined for a competitor test vial and compared to known test vial reference signals to determine that the competitor has copied a specific, known test vial sensor chemistry.

Implementations disclosed herein provide systems, methods and apparatus for optimizing detection of optical signals indicating the presence of an analyte of interest in a sample. One skilled in the art will recognize that these embodiments may be implemented in hardware, software, firmware, or any combination thereof.

In addition to the benefits described above, embodiments of the systems and methods described herein can be advantageously implemented without changing consumable components in current blood culture measurement systems. For example, implementations of the presently disclosed technology can be implemented without changing the assay bottle including its contents compromised of media, nutrient solution, and a sensor. Further, embodiments of the systems and methods described herein can be implemented with a one-time cost, which can be limited to the total cost of adding optical interrogation at specified wavelengths and a related algorithm code to process optical measurements and determine a reference signal as described herein.

It will be further understood that the embodiments of the disclosed technology are not limited to blood culture measurement systems, and can be applied to other types of optical detection systems that rely on sensors or other materials that have a non-varying characteristic suitable for use as a reference signal for normalization of detector readings, such as an isosbestic point. For example, in certain embodiments, the disclosed technology can be applied to immunoassays, including immunoassays in which the immunoassay is monitoring output as a function of time and immunoassays in which the immunoassay is a one point in time test (i.e., an episodic test). When the immunoassay is an episodic test, a ratio of the test output to the isosbestic point can be used as an assay quality indicator or as surveillance method indicating that an immunoassay has been copied or counterfeited.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the present disclosure. In other words, unless a specific order of steps or actions is required for proper operation of the method that is being described, the order and/or use of specific steps and/or actions may be modified without departing from the scope of the present disclosure.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use embodiments of the present disclosure. Various modifications to these implementations will be readily apparent to those skilled in the art, and the generic principles defined herein may be applied to other implementations without departing from the spirit or scope of the present disclosure. Thus, the present disclosure is not intended to be limited to the implementations shown herein but is to be accorded the widest scope consistent with the principles and novel features disclosed herein.

What is claimed is:

1. A method of determining the presence of an analyte of interest in a blood sample, the method comprising:
    introducing a reference fluid into a reference vial comprising a reference vial sensor comprising a fluorophore and a pH indicator;
    transmitting light at an excitation frequency of the reference vial sensor to the reference vial to cause the reference vial sensor to emit a reference vial fluorescence signal;
    filtering the reference vial fluorescence signal using a first emission filter and a second emission filter that is different than the first emission filter;
    measuring an intensity of the reference vial fluorescence signal that was filtered using the first emission filter and an intensity of the reference vial fluorescence signal that was filtered using the second emission filter to generate a reference ratio;
    inoculating a blood culture test vial comprising a test vial sensor with the blood sample, the test vial sensor comprising a fluorophore and a pH indicator;
    transmitting light at an excitation frequency of the test vial sensor to the test vial to cause the test vial sensor to emit a test vial fluorescence signal;
    filtering the test vial fluorescence signal using the first emission filter and the second emission filter;
    measuring an intensity of the test vial fluorescence signal that was filtered using the first emission filter and an intensity of the test vial fluorescence signal that was filtered using the second emission filter to generate a test vial ratio;

determining a pH state of the pH indicator of the test vial sensor by comparing the test vial ratio to the reference ratio, the pH state indicative of a pH of the blood sample; and determining the presence of the analyte of interest based on the determined pH state of the pH indicator of the test vial sensor, the analyte of interest comprising a microorganism.

2. A method of normalizing detector readings, the method comprising:

introducing a first reference fluid into a first reference vial comprising a first reference vial sensor comprising a fluorophore and a pH indicator, the first reference fluid exposing the first reference vial sensor in the first reference vial to a first performance boundary condition, the first performance boundary condition comprising a low pH condition or a high pH condition;

transmitting light at an excitation frequency of the first reference vial sensor to the first reference vial to cause the first reference vial sensor to emit a first reference vial fluorescence signal;

filtering the first reference vial fluorescence signal using a first emission filter and a second emission filter that is different than the first emission filter;

measuring an intensity of the first reference vial fluorescence signal that was filtered using the first emission filter and an intensity of the first reference vial fluorescence signal that was filtered using the second emission filter to generate a first reference ratio;

inoculating a blood culture test vial comprising a test vial sensor with the blood sample, the test vial sensor comprising a fluorophore and a pH indicator;

transmitting light at an excitation frequency of the test vial sensor to the test vial to cause the test vial sensor to emit a test vial fluorescence signal;

filtering the test vial fluorescence signal using the first emission filter and the second emission filter;

measuring an intensity of the test vial fluorescence signal that was filtered using the first emission filter and an intensity of the test vial fluorescence signal that was filtered using the second emission filter to generate a test vial ratio; and normalizing the measured intensity of the test vial fluorescence signal that was filtered using the first emission filter and the intensity of the test vial fluorescence signal that was filtered using the second emission filter by comparing the test vial ratio to the first reference ratio.

3. The method of claim 2, wherein the first reference ratio is generated by dividing the measured intensity of the first reference vial fluorescence signal that was filtered using the first emission filter by the measured intensity of the first reference vial fluorescence signal that was filtered using the second emission filter.

4. The method of claim 3, wherein the test vial ratio is generated by dividing the measured intensity of the test vial fluorescence signal that was filtered using the first emission filter by the measured intensity of the test vial fluorescence signal that was filtered using the second emission filter.

5. The method of claim 4, further comprising determining the pH state of the pH indicator of the test vial sensor by comparing the test vial ratio to the first reference ratio.

6. The method of claim 4, further comprising, prior to inoculating the blood culture test vial with the blood sample:

introducing a second reference fluid into a second reference vial comprising a second reference vial sensor comprising a fluorophore and a pH indicator, the second reference fluid exposing the second reference vial sensor in the second reference vial to a second performance boundary condition, wherein the first performance boundary condition is a low pH condition and the second performance boundary condition is a high pH condition;

transmitting light at an excitation frequency of the second reference vial sensor to the second reference vial to cause the second reference vial to emit a second reference vial fluorescence signal;

filtering the second reference vial fluorescence signal using the first emission filter and the second emission filter;

measuring an intensity of the second reference vial fluorescence signal that was filtered using the first emission filter and an intensity of the second reference vial fluorescence signal that was filtered using the second emission filter to generate a second reference ratio.

7. The method of claim 6, further comprising comparing the test vial ratio to a range of ratios bounded by the first reference ratio and the second reference ratio.

8. The method of claim 2, wherein the first emission filter is configured to filter a range of wavelengths of a fluorescence output spectrum of the fluorophore, and wherein the second emission filter comprises a narrow band pass filter configured to filter wavelengths at or near an absorbance peak of the pH indicator of the first reference vial sensor and the pH indicator of the test vial sensor.

9. The method of claim 1, wherein the reference ratio is generated by dividing the measured intensity of the reference vial fluorescence signal that was filtered using the first emission filter by the measured intensity of the reference vial fluorescence signal that was filtered using the second emission filter.

10. The method of claim 9, wherein the test vial ratio is generated by dividing the measured intensity of the test vial fluorescence signal that was filtered using the first emission filter by the measured intensity of the test vial fluorescence signal that was filtered using the second emission filter.

11. The method of claim 1, wherein the microorganism comprises bacteria.

* * * * *